United States Patent [19]

Lev et al.

[11] Patent Number: 5,403,462
[45] Date of Patent: Apr. 4, 1995

[54] ELECTROCHEMICAL ELECTRODES AND METHODS FOR THE PREPARATION THEREOF

[75] Inventors: Ovadia Lev; Michael Tsionsky, both of Jerusalem; Genia Gun, Rehovot; Victor Glezer, Jerusalem, all of Israel

[73] Assignee: Yissum Research Development Company of the Hebrew Univeristy of Jerusalem, Jerusalem, Israel

[21] Appl. No.: 80,520

[22] Filed: Jun. 24, 1993

[51] Int. Cl.⁶ ..................... G01N 27/26; C25B 11/04
[52] U.S. Cl. ................................. 204/403; 204/414; 204/416; 204/291; 204/290 R; 156/60; 156/308.2; 435/817
[58] Field of Search ................. 204/403, 290 R, 416, 204/414, 291; 156/308.2; 435/817; 23/295 F

[56] References Cited

U.S. PATENT DOCUMENTS 4,923,578  5/1990  Benton et al. ................. 204/180.9
5,001,453  3/1991  Ikejiri et al. ........................ 338/35

OTHER PUBLICATIONS

Brinker et al., "Sol–Gel Science", Academic Press, 1990, pp. 1–123 no month available.
G. Phillip and H. Schmidt, *J. of Non–Cyrstalline Solids*, vol. 63, p. 283, 1984 no month available.
H. Schmidt and H. Wolter, *J. of Non–Cyrstalline Solids*, vol. 121, p. 428, 1990 no month available.
J. E. Anderson et al., *Anal. Chem.*, vol. 61, pp. 2330–2332, 1989 no month available.
B. R. Shaw and K. E. Creasy, *Anal. Chem.*, vol. 60, pp. 1241–1244, 1988.
H. S. Swofford and R. L. Charman III, *Anal. Chem.*, vol. 38, pp. 966–969, 1966 no month available.
C. Urbanczky and K. Lundstrom, *J. Electroanal. Chem.*, vol. 176, pp. 169–182, 1984 no month available.
V. Glezer and O. Lev, *J. Am. Chem. Soc.*, vol. 115, p. 2533, 1993 no month available.
K. Kamiya et al., *J. of Non–Cyrstalline Solids*, vol. 199, pp. 14–20, 1990 no month available.
O. Lev, *Analyusis*, vol. 20, pp. 543–553, 1992 no month available.
A. Chatterjee and D. Chakravorty, *J. Phys. D. Appl. Phys.*, vol. 23, pp. 1097–1102, 1990 no month available.

*Primary Examiner*—Kathryn Gorgos
*Attorney, Agent, or Firm*—Foley & Lardner

[57] ABSTRACT

An electrochemical electrode, comprising carbon particles distributed in porous, inorganic ceramic material produced by sol-gel technology, wherein the particles form a continuous network which enables conductivity throughout the sol-gel derived matrices.

11 Claims, 5 Drawing Sheets

ELECTROCHEMICAL ELECTRODES AND METHODS FOR THE PREPARATION THEREOF

BACKGROUND OF THE INVENTION

1. Field of the Invention

The present invention relates to electrochemical electrodes and to methods for the preparation thereof. More particularly, the present invention relates to porous, conductive electrodes comprising carbon particles distributed in sol-gel-derived matrices. These sol-gel-derived silica-carbon composites can be used as inert electrodes, reference electrodes, or selective electrodes and for electrochemical catalysis and biosensing. The composite silica-carbon electrodes can be produced in the form of thin layers, monolithic rods or disks, and in the form of microelectrodes.

2. Description of the Related Art

The term "sol-gel technology" as used herein is a general name for the known process of production of silica and metal oxide ceramics by meltless processes through the polymerization of suitable monomers (such as the metal alkoxides), which produce colloidal suspension ("sol") and, upon further agglomeration, produce xerogel ("dry gel") or dry film states.

The term "sol-gel glass" as used herein relates to any ceramic or organoceramic material as depicted generally in C. J. Brinker and G. W. Scherer, *Sol-Gel Science*, Academic Press, San Diego, Calif., U.S.A., 1990, the teachings of which are incorporated herein by reference.

The term 'sol-gel process,' as used herein, is as defined and explained in C. J. Brinker and G. W. Scherer, *Sol-Gel Science*, discussed above, and is defined broadly as the preparation of ceramic materials by preparation of a sol, gelation of the sol, and removal of the solvent.

Most of the sol-gel techniques use low molecular weight tetraalkoxysilane precursors (mainly, tetramethoxysilane abbreviated as TMOS, or tetraethoxysilane abbreviated as TEOS), although it is also possible to use sodium silicate precursors. The overall chemical reaction is given by Equation 1:

$$Si(OR)_4 + (4-x)H_2O \rightarrow SiO_x(OH)_{4-2x} + 4ROH \qquad (1)$$

The reaction proceeds through hydrolysis (Equation 2, below), and condensation (Equation 3, below) steps:

Since alkoxysilane is not miscible in aqueous solution, methanol or another solvent (e.g., THF, alcohols) is frequently used for homogenization.

Unlike the polymerization of organic polymers that is governed by the formation of chain polymers, which branch and crosslink to form the gel, silica polymerization is believed to evolve mainly through the formation of a colloidal suspension (the sol), which gels by agglomeration. Since silica oligomers are silanol rich, the pH level strongly influences the kinetics of the agglomeration and the final structure of the xerogel. High pH conditions produce condensed particulate sols, which eventually agglomerate to give highly porous silica gels. Low pH (2-7) polymerization gives branched polymeric sols and dense, high surface area (up to about 1000 m³/gr) gels.

During the last stage of the gelation, water and solvent evaporate from the glass cavities, thus forming the dry gel (xerogel) state.

Often a high temperature sintering step is used to densify the porous layer and to form poreless films or monoliths. This step is omitted or used mildly in the preparation of the silica carbon composite electrodes of the present invention.

Using the sol-gel process, it is possible to produce ceramics in virtually any desired configuration, including thin films, powders, fibers and monoliths, and from various metal oxides such as titania, silica, alumina, vanadium oxide, and mixed oxides of different compositions.

By using a different type of precursors, it is possible to produce modified silica matrices with controlled surface properties. For example, a mixture of methyltrimethoxysilane (MTMOS) and tetramethoxysilane (TMOS) monomers gives:

Replacing the methyl group in the methyltrimethoxy with octadecyl or another radical ( such as phenyl, aminoalkyl or cyanoalkyl) alters the surface properties of the material (G. Philipp and H. Schmidt, *J. of Non-Crystalline Solids*, Vol. 63, p. 283, 1984; H. Schmidt and H. Wolter, *J. of Non-Crystalline Solids*, Vol. 121, p. 428, 1990).

Recently it was found, as described in pending U.S. patent application Ser. No. 07/637,873, that it is possible to entrap inorganic, organic and biological chemicals in sol-gel ceramics by incorporating them with the sol-gel precursors, and that these reagents can interact with diffusible solute or components in an adjacent liquid or gas phase. Hereinafter, these materials are referred to as "doped sol-gel glasses."

SUMMARY OF THE INVENTION

According to the present invention, it has now been found that by incorporating carbon particles along with the sol-gel polymerization precursors, it is possible to produce conductive silica-carbon composites where the carbon powder is held together by the porous silica network. It has further been found that the carbon particles still form a continuous network which enables global conductivity. Moreover, according to the present invention, the carbon powder remains exposed in the surface of the pores of the ceramic material and thus it is accessible to diffusible analytes and solvents and to chemicals that are embedded in the glass matrix (i.e., covalently bonded, impregnated or doped chemicals). This is particularly important, since it provides the carbon-silica electrodes with the improved conductivity of the carbon with the favorable characteristics of the inorganic supporting matrix such as inertness and rigidity, in addition to the specificity and catalytic activity of the immobilized reagents.

Thus, the present invention provides an electrochemical electrode comprising carbon particles distributed in porous inorganic ceramic material produced by sol-gel technology, wherein said particles form a continuous network which enables conductivity throughout said sol-gel-derived matrices.

The present invention also provides a process for the production of said composite silica-carbon electrodes by mixing silica or other metal oxide sol-gel precursors such as tetraethoxysilane or alkyltrimethoxysilane with graphite powder and acid or base catalyst and introducing the solution into a container with a desirable configuration. After a gelation and drying period (which takes between a few hours for a few micron films up to a few weeks for thick monoliths), a black solid electrode is formed in the configuration of the casting container. Typical electric resistance of such electrodes is approximately 1 ohm/cm. Glass shrinkage that usually takes place during the drying of sol-gel derived silica was insignificant during the formation of the carbon silica composite. Optimal weight ratio of the precursors were found to be 1.5 methanol: 1 trimethoxysilane:0.05 concentrated HCl:3.75 ultra pure carbon. The sol-gel mixture can include also other glass-forming precursors such as tetramethoxysilane, phenyltrimethoxysilane, ferrocene-carboxamide-3-propyl-trimethoxysilane. The sol-gel starting solution can include also other chemical dopants that do not participate in the polycondensation but remain immobilized in the composite carbon-silica matrix, such as inorganic (e.g., platinum chloride ); organic (e.g., ferrocene), or biochemical (glucose oxidase) compounds. Chemical modifiers such as silver chloride or quinone can be impregnated into a preformed carbon electrode in order to modify its chemical properties.

The present invention provides inert electrodes, reference electrodes and selective electrodes, as well as electrodes useful for electrochemical catalysis and electrochemical biosensing, as described and exemplified hereinafter.

Inert Electrodes

According to the present invention, it has now also been surprisingly found that by using hydrophobic glass-forming precursors (e.g., alkyltrimethoxysilane, 3-chloropropyltrimethoxysilane, chloromethyltriethoxysilane and diphenyldiethoxysilane) it is possible to produce conductive porous carbon-supported electrodes that repel water and thus exhibit excellent faradaic signal/background current characteristics. Such hydrophobic silica-carbon electrodes are useful for electro-analytical devices such as detectors for flow injection analyses and liquid chromatography. It was found that these electrodes withstand extreme pH conditions because only the external surface of the glass-carbon matrix can be wetted and become exposed to hydrolysis. Thus, the present invention preferably provides a sensing inert electrode, wherein hydrophobic glass-forming material is incorporated in the sol-gel precursors, thus forming a hydrophobic composite ceramic electrode.

Reference Electrodes

An ideal reference electrode is an electrode whose interfacial potential difference is constant regardless of the composition of the solution, and which is insensitive to the current. Therefore, high surface area, porous electrodes have an advantage. According to the present invention, it has now been found that by incorporating a redox couple into the composite glass-carbon matrix, it is possible to produce good porous reference electrodes, with an external surface which can be renewed by mechanical polishing. Thus, the present invention preferably provides an electrochemical reference electrode, wherein a redox couple is immobilized within the composite sol-gel carbon electrode, forming a reference electrode.

Selective Electrodes

An ideal selective electrode is an electrode whose current-potential (e.g., its rest potential versus a reference electrode or current response under given applied potential constraint) characteristics are influenced by the presence of a specific compound or a group of compounds. According to the present invention, it has now been found that by incorporation of compounds with specific affinity towards a target analyte (e.g., silver and potassium chloride) in the composite glass-carbon matrix, it is possible to produce selective electrodes (e.g., chloride-selective electrodes). The surface of said electrodes can be renewed by mechanical polishing without changing the response of the electrodes. Thus, the present invention also provides an electrochemical selective electrode, wherein a selective compound or functional group is immobilized within the composite sol-gel carbon electrode, thus forming a selective electrode.

Electrochemical Catalysis

Electrochemical catalysis is defined as changes in the potential of a heterogeneous electron transfer reaction, due to the presence of other chemical compounds in the vicinity of the electrode. According to the present invention, it has now been found that by incorporation of small amounts of catalysts (e.g., metallic palladium for hydrogen reduction step), electrochemical catalyses can be performed (e.g., hydrogen reduction at higher potentials, i.e., lower overvoltage). This implies that the catalyst, the carbon surface and the penetrating reactant can approach, close proximity within the porous carbon-silica composite.

Electrochemical Biosensing

An electrochemical biosensor is comprised of a membrane or a layer of enzymes that catalyzes the conversion of a target analyte. The products or by-products of this reaction are sensed by a heterogeneous charge transfer process at the conductive electrode. According to the present invention, it has now been found that incorporation of enzyme in the starting solution of the composite sol-gel carbon material process can produce carbon-Silica glass composite that can perform as an electrochemical sensor.

Related Techniques

Carbon composites, including, for example, carbon powders immobilized in poly(chlorotrifluoroethylene) (J. E. Anderson, D. Hopkins, J. W. Shadrick and Y. Ren, *Anal. Chem.*, Vol. 61, pp. 2330-2332, 1989); cross-linked polystyrene (B. R. Shaw and K. E. Creasy, *Anal. Chem.*, Vol. 60, pp. 1241-1244, 1988); epoxy (H. S. Swofford and R. L. Carman III, *Anal. Chem.*, Vol. 38, pp. 966-969, 1966); wax and nujol (C. Urbaniczky and K. Lundstrom, *J. Electroanal. Chem.*, Vol. 176, pp. 169-182, 1984) have been reported in the literature. However, in all these techniques the carbon powder is imbedded in organic materials, and thus, none of said publications teaches or suggests the advantages of the carbon-containing porous ceramic matrices of the present invention.

Doped sol-gel electrodes and biosensors were reported by Avnir and co-workers (U.S. patent application No. 07/637,873). Sol-gel-derived glucose enzyme electrodes made of vanadium pentaoxide doped with glucose oxidase enzyme were also recently reported (V. Glezer and O. Lev, *J. Am. Chem. Soc.*, Vol. 115, p. 2533, 1993). However, the vanadium oxide electrodes exhibit lower conductivity (approximately $10^{-4}$ ohm/cm) than the carbon-silica composite (approximately 1 ohm/cm) of the present invention, and silica sol-gel-derived matrices are not conductive at all.

Sol,gel-derived carbon-silica composites were reported by Kamiya, et al. (K. Kamiya, T. Yoko, T. Sano and K. Tanaka, *J. of Non-Crystalline Solids*, Vol. 119, pp. 14–20, 1990). These materials are made by pyrolysis of xerogels containing traces or organic materials, thus forming homogeneous distribution of nanoparticles embedded in the sol-gel matrices. Because of the high temperature of the pyrolysis step, this type of material cannot be doped with organic or heat-sensitive materials, and covalently-bonded organic reactants decompose during the heat treatment. Finally, electrochemical applications of these materials have never been proposed, and the low surface area created therein would render such matrices substantially inferior to the highly porous electrodes of the present invention.

As indicated, the carbon-silica composites of the present invention combine the benefits of a carbon-conductive network with the advantages of a porous ceramic matrix. Thus, the newly-proposed silica-carbon composite electrodes of the present invention offer the following advantages:

a. high electric conductivity (approximately 1 ohm/cm);
b. high temperature stability;
c. rigid structure that does not swell in aqueous and organic solvents;
d. control over the physical configuration of the electrode, including manufacture of thin films, monolithic disks or rods, and even microelectrodes;
e. control over pore size distribution (thus providing selectivity due to size exclusion. phenomena);
f. control over the hydrophobicity of the glass-carbon electrode (thus providing a possibility to produce inert electrodes with small background current density due to exclusion of water from the porous network, and a possibility to produce a porous high surface-area catalyst when hydrophilic glass-forming procedures are used);
g. the ability to entrap or immobilize organic, inorganic or biochemical substances in close proximity to the conducting surface by impregnation, doping or covalent bonding;
h. easy surface renewal by mechanical polishing; and
i. simplicity of preparation.

As inert electrodes, the silica-carbon composite materials offer higher stability compared with paste electrodes, and their surface can be easily renewed, which provides an advantage over glassy carbon electrodes. For catalytic, biosensing and reference electrode applications, the composite sol-gel carbon electrodes of the present invention offer porous structure having a polishable external surface and higher surface area than the paste and glassy carbon electrodes heretofore proposed and made available by the prior art.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the above-mentioned attached figures, the following should be viewed as captions therefor:

FIG. 1: Response of: (a) a composite carbon sol-gel electrode; (b) a glassy carbon electrode; (c) carbon rod electrode; (d) carbon paste electrode, immersed in (1) 1M HCl and (2) 1M HCl+1 mM $K_3Fe(CN)_6+K_4Fe(CN)_6$ solution.

Figure 1A:
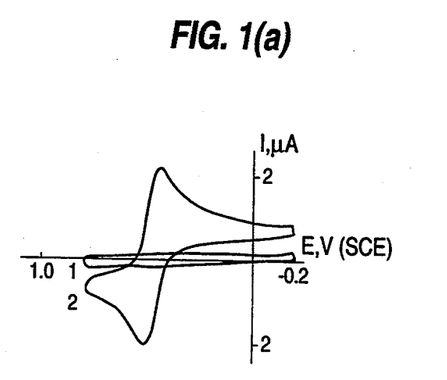
FIG. 1 depicts the cyclic voltammogram of four types of carbon electrodes.
Figure 1B:
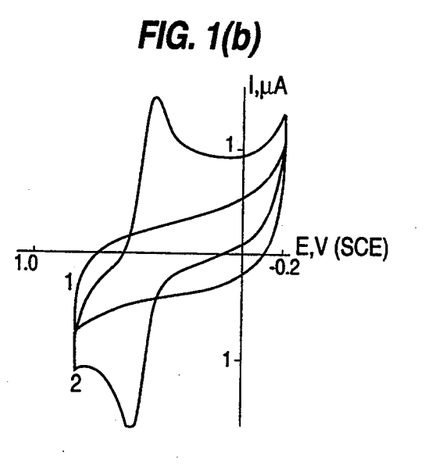
Figure 1C:
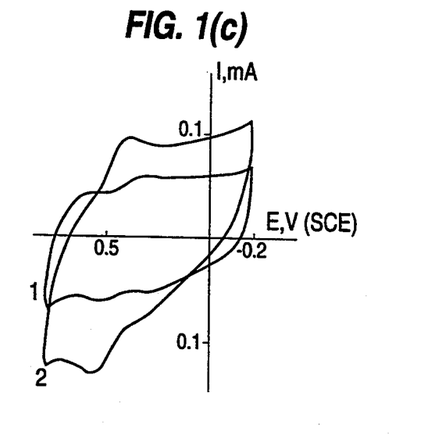
Figure 1D:
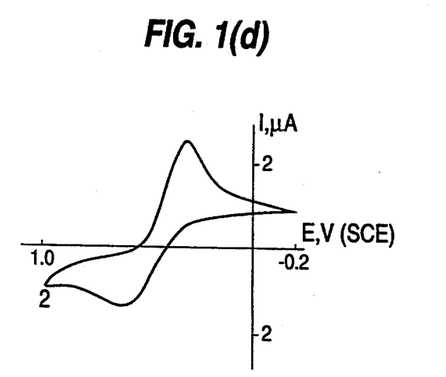
Figure 2A:
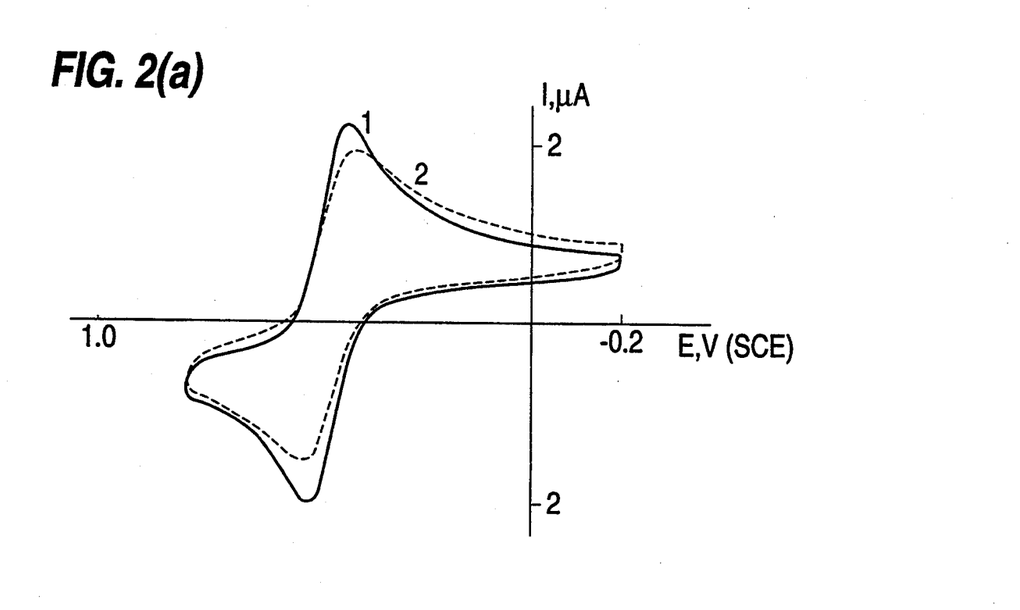
FIGS. 2a and 2b depict the cycling voltammograms of a composite sol-gel carbon electrode and a carbon paste in 1M HCl+1.0 mM $K_3Fe(CN)_6+K_4Fe(CN)_6$ solution.
Figure 2B:
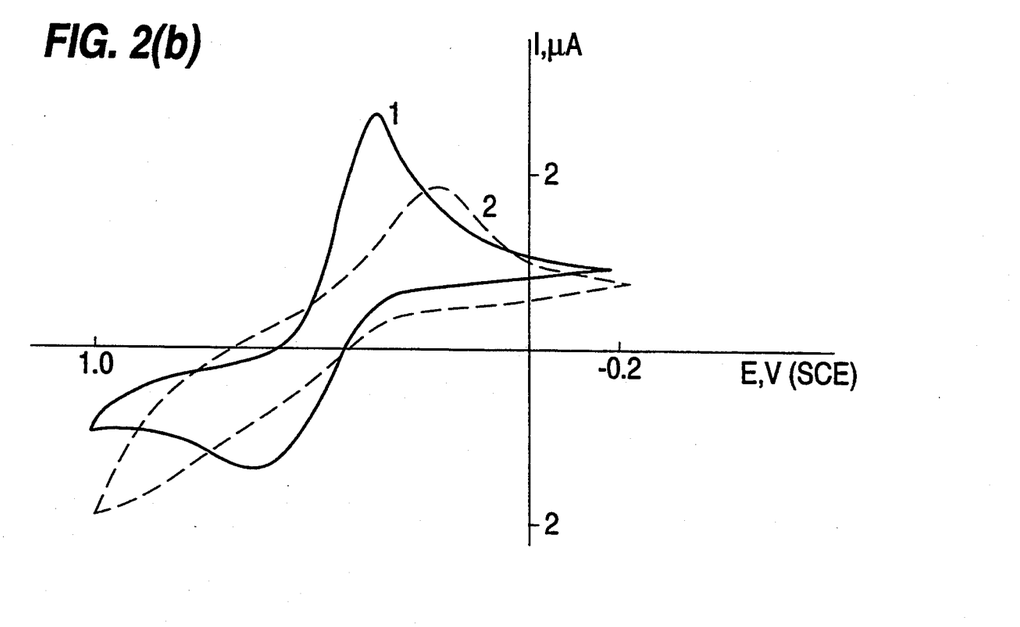

FIGS. 2a and 2b: Response of: (a) a composite carbon sol-gel electrode and (b) a carbon paste electrode, in 1M HCl+1 mM $K_3Fe(CN)_6+K_4Fe(CN)_6$ solution, (1) immediately after immersion and (2) after a 24-hour period.

Figure 3:
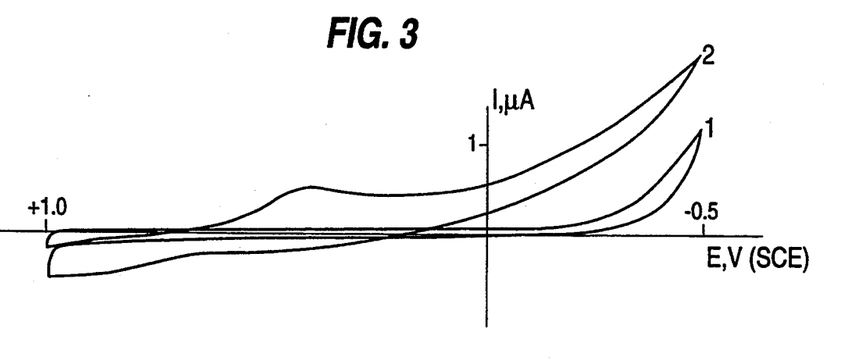
FIG. 3 depicts the cyclic voltammograms of a composite sol-gel carbon electrode and a palladium-modified composite sol-gel carbon electrode immersed in 3M $H_2SO_4$ solution.

FIG. 3: Cyclic voltammograms (scan rate=100 mV/sec) of (1) a composite sol-gel carbon electrode and (2) a composite palladium modified sol-gel carbon electrode, immersed in 3M $H_2SO_4$ solution.

Figure 4:
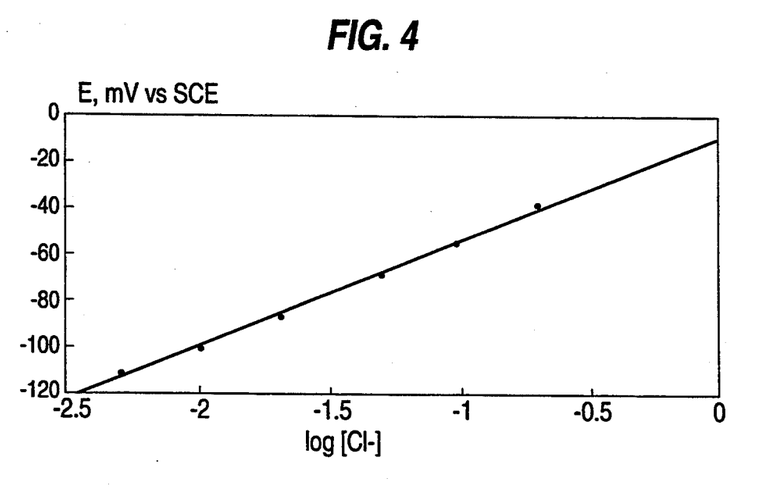
FIG. 4 illustrates the electrode potential of a silver/silver chloride-modified composite sol-gel carbon electrode.

FIG. 4 Potential response of a silver/silver chloride modified composite silica carbon reference electrode exposed to different concentrations of potassium chloride.

Figure 5:
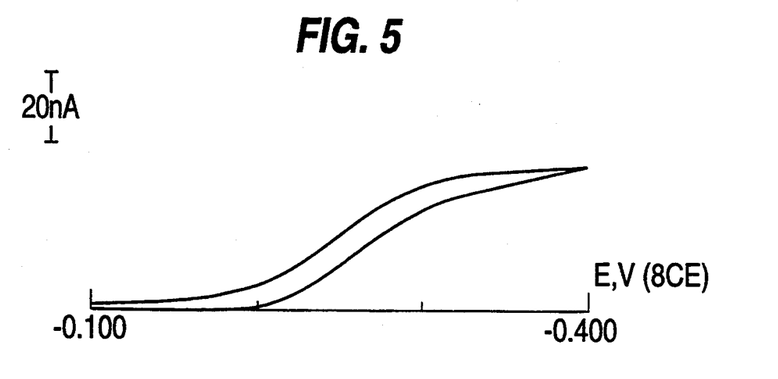
FIG. 5 demonstrates a cyclic volammogram (scan rate=50 mV/sec) of 5.0 mM hexamine ruthenium (II) chloride (STEM Chemicals) in 0.2 acetate buffer (pH=4.7) and 0.3M sodium sulfate, the shape of the voltammogram and the level of the saturation current indicating a configuration of a microelectrode with approximately 20 $\mu$M radius.

FIG. 5 Cyclic voltammogram of microcomposite silica carbon electrode in 5.0 mM hexamine ruthenium (II) chloride solution (pH=4.7; scan rate=50 mV/sec).

Figure 6:
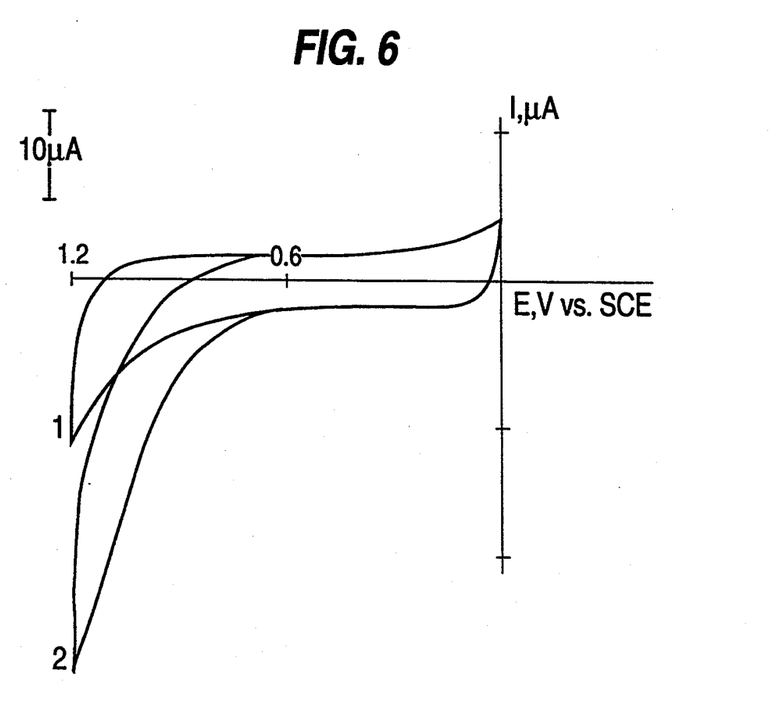
FIG. 6 depicts the cycling voltammetric curves (scan rate=100 mV/sec) of a carbon composite electrode immersed in a blank solution (buffered at pH=5.6 by phosphate buffer) and in 9.8 mM glucose solution, the increased anodic current which becomes apparent at approximately 700 mV/SCE being caused by oxidation of the hydrogen peroxide that was formed during the enzymatic conversion of glucose to gluconolactone.

FIG. 6 Cyclic voltammogram of composite carbon-silica glucose biosensor exposed to (1) a blank solution;

and (2) 9.8 mM glucose (scan rate=100 mV/sec; pH=5.6).

Figure 7:
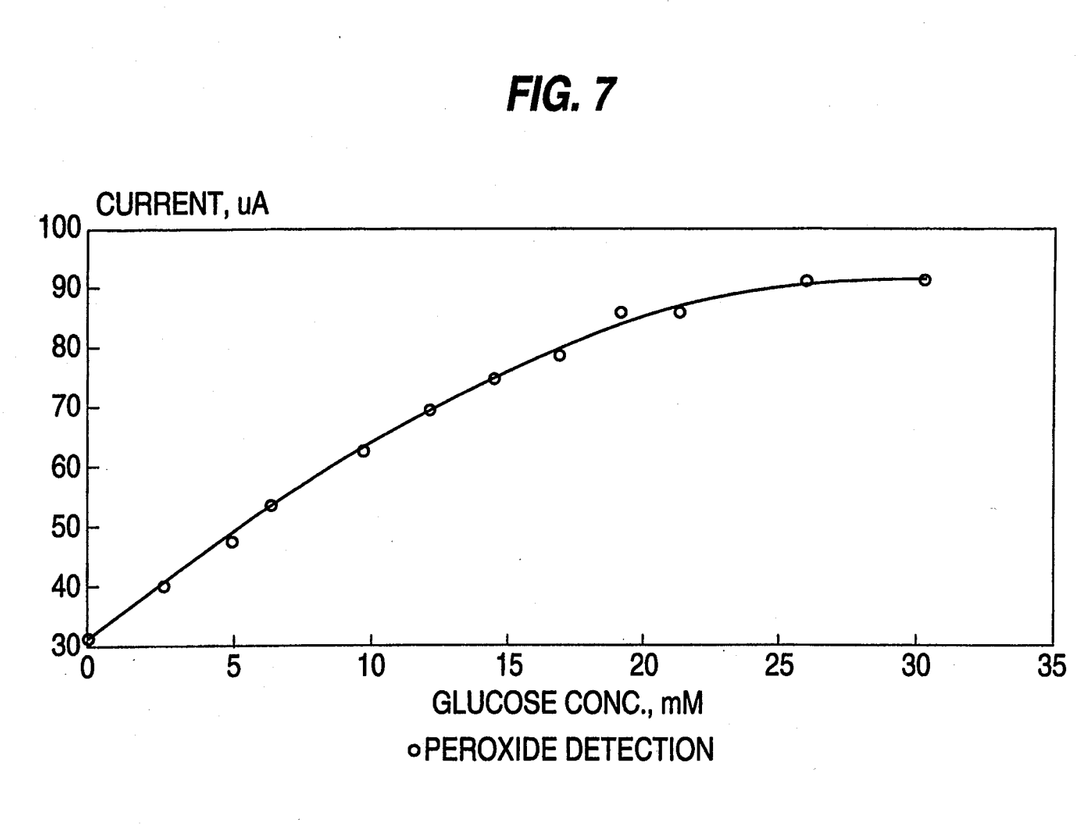
FIG. 7 demonstrates a typical glucose calibration curve, depicting the dependence of the current at 1.2 V vs. saturated calomel electrode (SCE) vs. glucose concentration (other parameters are the same as in FIG. 6).

FIG. 7 A calibration curve of composite carbon-silica glucose biosensor (scan rate=100 mV/sec; pH=5.6; E=1.2 V/sce).

DESCRIPTION OF THE PREFERRED EMBODIMENTS

Example 1

A Comparison of Capacitive Currents of Typical Carbon Electrodes

Preparation of carbon sol-gel composite electrode:

1.5 ml methanol (Fluka), 0.5 ml methyltrimethoxysilane (Fluka) and 0.05 ml hydrochloric acid (11M) were mixed for 2 minutes, 3.75 g carbon powder (Ultra Carbon corporation) was added and shaken for an additional 1 minute. A 3 mm length of a 1 mm diameter capillary was filled with the sol-gel carbon mixture. The mixture was dried overnight in ambient conditions, yielding a dry conductive composite carbon sol-gel matrix. The electrode was polished with Emery paper before use. The conductivity of such a composite material was approximately 1.0 ohm/cm.

Preparation of glassy carbon electrode:

3 mm in diameter glassy carbon rod was purchased from Atomergic Chemicals. A glassy carbon tube was placed in a glass tube and sealed by Torr Seal epoxy. The electrode was polished with Emery paper and 0.05 μm alumina powder.

Preparation of carbon paste electrode:

0.3 g carbon powder (Ultra Carbon Corporation) was mixed with 0.1 g paraffin oil and filled into a 0.3 cm diameter glass capillary.

Preparation of carbon granite rod electrode:

A carbon granite rod (1.27 cm in diameter) (Alfa Products) was sealed in epoxy and polished with Emery paper and 0.05 μm alumina powder.

FIG. 1 depicts the cyclic voltammogram (scan rate=100 mv/sec) of the following four types of carbon electrodes immersed in 1M HCl and in 1M HCl+1 mM $K_3Fe(CN)_6 + K_4Fe(CN)_6$ solution: (a) a composite carbon sol-gel electrode; (b) a glassy carbon electrode; (c) a carbon rod electrode; and (d) a carbon paste electrode. The almost reversible oxidation and reduction waves of the redox couple are observed in all four electrodes. FIG. 1A clearly demonstrates that it is possible to apply a composite carbon electrode as a sensing electrode. Table I compares the observed capacitance, calculated by Equation (5), of these four electrodes:

$$C_{obs} = i/v\,A \quad (5)$$

wherein:

$C_{obs}$ = observed capacitance (Farad/cm$^2$);
i = average of the absolute cathode and anode current at 400 mV versus calomel electrode (Amperes);
v = scan rate (volts/see); and
A = electrode area (cm$^2$).

Despite the porous structure of the composite sol-gel carbon electrode, its observed capacitance is lower than that of glassy carbon and carbon rod electrodes.

TABLE I

| Observed Capacitance of Inert Carbon Electrodes | |
|---|---|
| Type of Electrode | Observed Capacitance (μF/mm$^2$) |
| Glassy carbon | 3.6 |
| Carbon rod | 500.0 |
| Carbon paste | 0.04 |
| Composite sol-gel carbon | 1.0 |

Observed in 1 M HCl, 100 mV/sec

Example 2

Comparison of the Stability of Carbon Paste and Composite Sol-Gel Carbon Electrodes Here, we illustrate the superior stability of the composite carbon electrode compared with the carbon paste electrode. The two electrodes were prepared according to the preparation procedures described in Example 1 above. FIGS. 2a and 2b depict the cycling voltammograms of a composite sol-gel carbon electrode and a carbon paste electrode in 1M HCl+1 mM $K_3Fe(CN)_6 + K_4Fe(CN)_6$ solution. The voltammograms were taken immediately after electrode immersion in the solution and after a 24-hour period. The paste electrode lost stability, exhibited high capacitive current and irreversible behavior after 24-hour immersion, while the composite electrode retained its original response.

Example 3

Electrochemical Catalysis

Preparation of the palladium modified composite sol-gel carbon electrode:

0.017 g $PdCl_2$ (Riedel) was dissolved in 1.5 ml methanol 0.1 ml HCl (11M) and mixed with 0.5 ml methyltrimethoxysilane (Fluka). An amount of 3.75 g carbon powder (Ultra Carbon Corporation) was added and shaken for an additional 1 minute. A 3 mm length of 1 mm diameter glass capillary was filled with this mixture and dried overnight in ambient conditions. The composite dry sol-gel carbon electrode was exposed to 100 atmosphere hydrogen gas for 1.0 hour in order to produce metallic palladium.

FIG. 3 depicts the cyclic voltammograms (scan rate=100 mV/sec) of a composite sol-gel carbon electrode prepared according to the protocol of Example 1, (shown as curve 1) and a palladium modified composite sol-gel carbon electrode immersed in 3M $H_2SO_4$ solution (shown as curve 2). The cathodic wave corresponding to hydrogen evolution starts at 0.1 V/sce and only at 0.2 V/sce on the composite sol-gel carbon electrode. The palladium modified sol-gel electrode retained its hydrogen evolution characteristics, even after surface renewal by polishing with Emery paper. Palladium-coated glassy carbon electrodes lose their catalytic activity when the metal layer is removed after a similar polishing treatment.

Example 4

Composite Sol-Gel Carbon Reference Electrodes

Electrode preparation:

0.0118 g silver nitrate was dissolved in 1.5 ml methanol, 0.5 ml tetramethoxysilane and 0.05 ml $HNO_3$ (60%) solution. An amount of 3.75 g carbon powder (Ultra Carbon Corporation) was added, and the mixture was shaken for 1 minute. A 3 mm length of a 1 mm diameter capillary was filled with the sol-gel carbon mixture. The mixture was dried overnight in ambient conditions, yielding a black, porous, dry and conductive electrode.

The electrode was soaked in 2.5M silver nitrate solution for one hour, dried for approximately 12 hours, then soaked in 6M aqueous hydrazine solution for 30 minutes in order to reduce the silver, and dried for an additional 12 hours. When this electrode was immersed in 0.2M sodium chloride solution, its potential was stable at $38 \pm 3$ mV relative to a saturated calomel electrode. A pH change over the range 2-10 did not affect the electrode response. The electrode retained its signal, even after surface renewal by polishing with Emery paper, demonstrating that the porous electrode is modified by the silver/silver chloride compounds, and not only its external surface.

Example 5

Composite Sol-Gel Carbon Selective Electrodes

In the following we demonstrate that the silver/silver chloride modified composite sol-gel carbon electrode can be used as a chloride selective electrode.

Electrode preparation:

The electrode was prepared according to the preparation protocol of Example 4.

FIG. 4 illustrates the electrode potential of the silver/silver chloride modified composite sol-gel carbon electrode. The electrode exhibits a logarithmic concentration-potential response. The electrode maintained its selectivity, even after rigorous polishing with Emery paper, demonstrating that its bulk was modified with the silver/silver chloride couple and not only its upper surface.

Example 6

Preparation of Composite Carbon Microelectrode

An amount of 1.5 ml methanol (Fluka), 0.5 ml methyltrimethoxysilane (Fluka) and 0.05 ml hydrochloric acid (11M) were mixed for 2 minutes, then 3.75 g crushed carbon powder (Ultra Carbon Corporation) was added and shaken for an additional 1 minute. Glass capillary was pulled by a micropipette puller in order to produce a tapered narrow capillary end. The thick end of the capillary was dipped into the paste of the sol-gel precursors. The glass capillary was centrifuged in order to push the sol-gel precursors into the narrow tip of the capillary. Finally, the microelectrode was allowed to gel and dry overnight in ambient conditions. Electrical contact was made by silver paint (Bio-Rad, A1208 Q-D colloidal silver). FIG. 5 illustrates that the electrode exhibits a response typical of microelectrode with appp. 12 $\mu$m radius.

Example 7

Carbon Composite Glucose Biosensor

Electrode preparation: 100 mg carbon powder (Ultra Carbon Corporation) was mixed with 0.5 ml aqueous solution containing 25 mg glucose oxidase (EC 1.1.3.4 type III's from Aspergillus Niger, Sigma Chemicals Co.). Approximately 0.05 ml suspension was applied on the surface of a glassy carbon electrode (prepared according to the protocol of Example 1). After drying for 2-3 hours, the carbon layer was immobilized by application of approximately 0.02 ml of a freshly prepared solution containing the sol-gel precursors. The solution contained 1.5 ml methanol, 0.5 ml tetramethoxysilane and 0.020 ml of concentrated HCl. The electrode was allowed to gel and dry in ambient conditions for a few hours before use.

FIG. 6 depicts the cyclic voltammetric curves (scan rate=100 mV/sec) of a carbon composite electrode immersed in a blank solution (buffered at pH=5.6 by phosphate buffer (as shown in curve 1), and in 9.8 mM glucose solution (as shown in curve 2), the increased anodic current which becomes apparent at approximately 700 mV/SCE being caused by oxidation of the hydrogen peroxide that was formed during the enzymatic conversion of glucose to gluconolactone; and FIG. 7 demonstrates a typical glucose calibration curve, depicting the dependence of the current at 1.2 V vs. saturated calomel electrode (SCE) vs. glucose concentration (other parameters are the same as in FIG. 6).

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are, therefore, intended to be embraced therein.

What is claimed is:

1. An electrochemical electrode, comprising carbon particles distributed in an inorganic ceramic, porous, sol-gel derived matrix material, and a dopant selected from the group consisting of a redox couple and a selective compound or functional group immobilized within the sol-gel derived matrix, wherein said carbon particles form a continuous network within said sol-gel derived matrix which enables conductivity throughout said matrix.

2. An electrochemical electrode according to claim 1, wherein a carbon sol-gel composite is deposited on a solid support material selected from the group consisting of organic and inorganic support surfaces.

3. An electrochemical electrode according to claim 1, wherein said inorganic ceramic material is a metal oxide or mixture of oxides.

4. An electrochemical electrode according to claim 1, wherein said inorganic ceramic material is selected from the group consisting of silica, titania, alumina, and a mixture thereof.

5. An electrochemical reference electrode made according to claim 1, wherein said dopant is a redox couple immobilized within said composite sol-gel carbon electrode, forming a reference electrode.

6. An electrochemical selective electrode made according to claim 1, wherein said dopant is a selective compound or functional group immobilized within the composite sol-gel carbon electrode, thus forming a selective electrode.

7. A process for preparing an electrochemical electrode as claimed in claim 1, comprising:
mixing carbon powder with a solution containing precursors of the sol-gel process;
allowing said mixture to gel and dry at temperatures that are lower than temperatures causing pyrolysis; and
incorporating said dopant into said matrix by adding said dopant to said solution containing sol-gel precursors or impregnating said dopant into said matrix, whereby a composite sol-gel carbon electrode, having carbon particles forming a continuous network distributed therein and said dopant immobilized therein is produced.

8. A process according to claim 7, wherein said precursor of the sol gel process are applied to a fixed bed or layer of carbon powder, thus forming a dispersion of the carbon powder in the resulting sol-gel-derived porous glass.

9. An electrochemical electrode, comprising:
  (a) a porous, inorganic ceramic xerogel matrix shaped in the configuration of an electrode; and
  (b) carbon particles distributed throughout said xerogel matrix to form a continuous network within said matrix, which enables conductivity throughout said matrix; and
  (c) a dopant selected from the group consisting of a redox couple and a selective compound or functional group immobilized within the xerogel matrix carbon electrode.

10. An electrochemical reference electrode made according to claim 9, wherein said dopant is a redox couple immobilized within the xerogel carbon electrode, thus forming a reference electrode.

11. An electrochemical selective electrode according to claim 9, wherein said dopant is a selective compound or functional group immobilized within the xerogel carbon electrode, thus forming a selective electrode.

* * * * *